US00PP12486P2

(12) United States Plant Patent
Westhoff

(10) Patent No.: US PP12,486 P2
(45) Date of Patent: Mar. 26, 2002

(54) CALIBRACHOA PLANT NAMED 'WESPINK'

(75) Inventor: Heinrich Westhoff, Südlohn-Oeding (DE)

(73) Assignee: Gartenbau and Spezialkulturen Westhoff GbR, Sudlohn-Oeding (DE)

( * ) Notice: Subject to any disclaimer, the term of this patent is extended or adjusted under 35 U.S.C. 154(b) by 0 days.

(21) Appl. No.: 09/592,377

(22) Filed: Jun. 12, 2000

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database, GTI JOUVE retrieval software 2001/01, citation for 'Wespink'.*

* cited by examiner

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Calibrachoa plant named 'Wespink', characterized by its cascading habit, rounded and spherical plant shape; freely and continuous branching habit; small, narrow leaves; vigorous growth habit; flowers that do not close with low light levels or at night; numerous intense purple-colored flowers; and good weather tolerance.

1 Drawing Sheet

BACKGROUND OF THE INVENTION

The present Invention relates to a new and distinct cultivar of Calibrachoa plant, botanically known as Calibrachoa sp., and hereinafter referred to by the cultivar name Wespink.

The new Calibrachoa is a product of a planned breeding program conducted by the Inventor in Sudlohn-Oeding, Germany. The new Calibrachoa originated from a cross made by the Inventor of the Calibrachoa cultivar Carillon Pink, not patented, as the female, or seed, parent with the Calibrachoa cultivar Million Bells Pink, not patented, as the male, or pollen, parent. The new Calibrachoa was selected by the Inventor in 1998 on the basis of its large flowers.

Asexual reproduction of the new cultivar by terminal cuttings taken at Sudlohn-Oeding, Germany, has shown that the unique features of this new Calibrachoa are stable and reproduced true to type in successive generations.

SUMMARY OF THE INVENTION

Plants of the cultivar Wespink have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Wespink'. These characteristics in combination distinguish 'Wespink' as a new and distinct cultivar:

1. Cascading habit, rounded and spherical plant shape.
2. Freely and continuous branching.
3. Small, narrow leaves.
4. Vigorous growth habit.
5. Flowers do not close with low light levels or at night.
6. Numerous intense purple-colored flowers.
7. Good weather tolerance.

Plants of the cultivar Wespink is most similar to the female parent, the cultivar Carillon Pink. However in side-by-side comparisons conducted by the Inventor in Sudlohn-Oeding, Germany, plants of the cultivar Wespink and the cultivar Carillon Pink differ in the following characteristics:

1. Plants of the new Calibrachoa have larger flowers than plants of the cultivar Carillon Pink.
2. Flower color of plants of the new Calibrachoa is more intense purple than flower color of plants of the cultivar Carillon Pink.
3. Flower throat color of plants of the new Calibrachoa is more intense yellow than flower throat color of plants of the cultivar Carillon Pink.
4. Petals of the new Calibrachoa have obtuse apices whereas petals of the cultivar Carillon Pink have emarginate apices.
5. Flowers of the new Calibrachoa do not close under low light conditions or at night whereas flowers of the cultivar Carillon Pink close under low light conditions and at night.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Calibrachoa. The photograph comprises a close-up view of typical flowers and leaves of 'Wespink'.

DETAILED BOTANICAL DESCRIPTION

In the following description, color references are made to The Royal Horticultural Society Colour Chart except where general terms of ordinary dictionary significance are used. Plants grown in greenhouses under long day conditions were used for the following description. Plants were grown under conditions which closely approximate commercial production conditions during the spring in Sudlohn-Oeding, Germany. During the production of the plants, day temperatures ranged from 20 to 26° C., night temperatures ranged from 16 to 18° C., and light levels ranged from 3,000 to 5,000 lux. Plants used for the description were about 20 weeks old.

Botanical classification: Calibrachoa sp. cultivar Wespink.

Parentage:

*Female parent.*—Calibrachoa sp. cultivar Carillon Pink, not patented.

*Male parent.*—Calibrachoa sp. cultivar Million Bells Pink, not patented.

Propagation:

*Type cutting.*—Terminal vegetative cuttings.

*Time to develop roots.*—About two weeks at 18 to 20° C.

*Root description.*—Numerous, fine, fibrous, and well-branched.

Plant description:

*Form.*—Annual flowering plant; initially upright, then cascading; uniform, rounded appearance, plants eventually become spherical in overall shape. Freely and continuous branching with lateral branches potentially forming at every node.

*Usage.*—Appropriate for hanging baskets, window boxes and patio containers.

*Crop time.*—About 8 weeks are required to produce finished flowering plants in 10-cm containers.

*Plant height* (*from soil level to top of plant plane*).—About 18 cm.

*Plant length* (*from soil level to lateral branches apices*).—About 92.5 cm.

*Plant diameter* (*area of spread*).—About 64 cm.

*Vigor.*—Vigorous growth habit.

*Stem description.*—Main branches, length: About 90 cm. Main branches, diameter: About 3 mm. Lateral branches, length: About 47 cm. Lateral branches, diameter: About 1.8 mm. Internode length: About 2.2 cm. Texture: Very short and fine pubescence. Color: 144A to 144B.

*Foliage description.*—Leaves simple, small, generally symmetrical and long persisting; sessile. Arrangement: Alternate. Length: About 2.5 cm. Width: About 8 mm. Shape: Oblanceolate. Apex: Rounded. Base: Attenuate. Margin: Entire. Aspect: Mostly flat. Texture: Smooth, somewhat leathery; slightly pubescent. Color: Young foliage, upper surface: 146A to 146B. Young foliage, lower surface: 147B. Mature foliage, upper surface: 147B. Mature foliage, lower surface: 148B.

Flower description:

*Flower type and habit.*—Small to medium-sized flowers; flowers face mostly outwardly; single, axillary. Flowers not persistent. Freely flowering.

*Natural flowering season.*—Spring until frost in the autumn; flowering continuous.

*Flower longevity on the plant.*—About one week.

*Flower size.*—Diameter: About 3.2 cm. Depth (height): About 1.7 cm. Tube length: About 1.7 cm. Throat diameter, distal end: About 1 cm. Tube diameter, proximal end: About 2.5 mm.

*Flower buds* (*just showing color*).—Length: About 2 cm. Diameter: About 5 mm. Shape: Oblong. Color: Apex, 77A; mid-section, 11C, with veins, 77A; base, 11C.

*Corolla.*—Arrangement/appearance: Single whorl of five petals, fused into flared trumpet. Petal length from throat: About 1.3 cm. Petal width: About 1.4 cm. Petal shape: Roughly spatulate with obtuse apex. Petal margin: Entire. Petal texture: Smooth, satiny. Color: Petal, upper surface, when opening: 74A. Petal, lower surface, when opening: 77C. Petal, upper surface, opened flower: 74A, fading to 78A; veins, 77A. Petal, lower surface, opened flower: 77B to 77C; veins, 77A. Flower throat (inside): 12B to 12D; some veining, 146C. Flower tube (outside): 13D; veins, 166A and 78B. Flower eye: Ring, 83B, with veins, 83A, about 3 mm in diameter at top of throat.

*Sepals.*—Arrangement/appearance: Single whorl of five sepals, star-shaped. Length: About 1.5 cm. Width: About 3 mm. Shape: Narrowly lanceolate. Apex: Acute to rounded. Margin: Entire. Texture: Smooth. Color, both surfaces: 146B to 146C.

*Peduncles.*—Length: About 1.35 cm. Width: About 1 cm. Strength: Flexible and wiry, flowers held mostly outwardly. Color: 144A with anthocyanin, 166A, near sepals.

*Reproductive organs.*—Stamens: Quantity: About five. Anther shape: Four-parted, oval. Anther length: About 1.5 mm. Anther color: 10B. Filament color: 144B to 144C. Pollen amount: Moderate. Pollen color: 10A to 10C. Pistils: Quantity: One. Pistil length: About 9 mm. Stigma shape: Oval. Stigma color: 144A. Style length: About 6.5 mm. Style color: 144B. Ovary color: 144B.

*Seed.*—Seed production has not been observed.

Disease resistance: Plants of the new Calibrachoa have not been noted to be resistant to pathogens common to Calibrachoa.

Weather tolerance: Plants of the new Calibrachoa are tolerant to rain and wind. Plants of the new Calibrachoa have been observed to tolerate temperatures from −3 to at least 30° C.

It is claimed:

1. A new and distinct cultivar of Calibrachoa plant named 'Wespink', as illustrated and described.

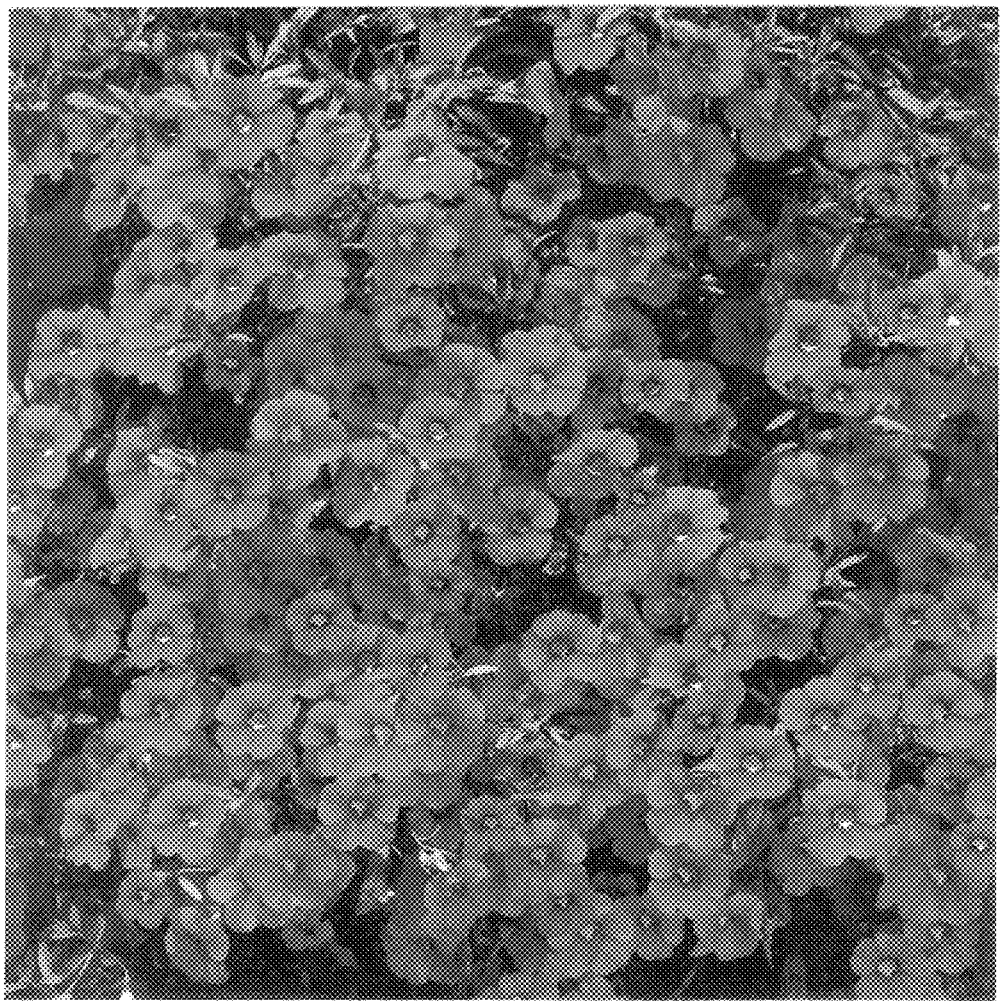

* * * * *